(12) United States Patent
Lewington et al.

(10) Patent No.: US 6,524,810 B2
(45) Date of Patent: Feb. 25, 2003

(54) METHOD OF MAKING BIOLUMINESCENT ASSAY REAGENT BASED ON NON-VIABLE E. COLI

(75) Inventors: Jay Lewington, Bisley (GB); Katherine Isles, Oxon (GB); Sandy Primrose, High Wycombe (GB)

(73) Assignee: Azur Environmental, Carlsbad, CA (US)

( * ) Notice: Subject to any disclaimer, the term of this patent is extended or adjusted under 35 U.S.C. 154(b) by 0 days.

(21) Appl. No.: 09/728,320

(22) Filed: Dec. 1, 2000

(65) Prior Publication Data

US 2001/0031492 A1 Oct. 18, 2001

Related U.S. Application Data

(63) Continuation of application No. PCT/GB99/01730, filed on Jun. 1, 1999.

(30) Foreign Application Priority Data

Jun. 2, 1998 (GB) .............................................. 9811845

(51) Int. Cl.⁷ .......................... G01N 33/52; C12Q 1/66; C12N 1/21

(52) U.S. Cl. ........................ 435/40.5; 435/8; 435/252.3; 435/252.33

(58) Field of Search ........................ 435/40.5, 8, 252.3, 435/252.33

(56) References Cited

U.S. PATENT DOCUMENTS

| 4,581,335 A | 4/1986 | Baldwin .................. 435/172.3 |
| 5,827,678 A | 10/1998 | Hesslewood et al. ......... 435/29 |

FOREIGN PATENT DOCUMENTS

WO    WO 9507346    3/1995

OTHER PUBLICATIONS

Biosis Abstract No. 199598122373, "Genetic changes and bioassays in bleomycin– and phleomycin–treated cells, and their relationship to chromosomal breaks", McKay, Judith F. et al., from *Mutation Research 336(1)*: p. 19–27, 1995.

*Primary Examiner*—Elizabeth Slobodyansky
(74) *Attorney, Agent, or Firm*—Kilpatrick Stockton LLP

(57) ABSTRACT

A cell-derived assay reagent prepared from cells which have been killed by treatment with an antibiotic selected from the bleomycin-phleomycin family of antibiotics but which retain a signal-generating metabolic activity such as bioluminescence.

8 Claims, 8 Drawing Sheets

METHOD OF MAKING BIOLUMINESCENT ASSAY REAGENT BASED ON NON-VIABLE E. COLI

This application is a continuation of PCT/GB99/01730, filed Jun. 1, 1999 designating the United States (the disclosure of which is incorporated herein by reference) and claiming priority from British application serial no. 9811845.8, filed Jun. 2, 1998.

FIELD OF THE INVENTION

The invention relates to a cell-derived assay reagent, in particular to an assay reagent prepared from cells which have been killed but which retain a signal-generating metabolic activity such as bioluminescence and also to assay methods using the cell-derived reagent such as, for example, toxicity testing methods.

BACKGROUND OF THE INVENTION

The use of bacteria with a signal-generating metabolic activity as indicators of toxicity is well established. UK patent number GB 2005018 describes a method of assaying a liquid sample for toxic substances which involves contacting a suspension of bioluminescent microorganisms with a sample suspected of containing a toxic substance and observing the change in the light output of the bioluminescent organisms as a result of contact with the suspected toxic substance. Furthermore, a toxicity monitoring system embodying the same assay principle, which is manufactured and sold under the Trade Mark Microtox®, is in routine use in both environmental laboratories and for a variety of industrial applications. An improved toxicity assay method using bioluminescent bacteria, which can be used in a wider range of test conditions than the method of GB 2005018, is described in International patent application number WO 95/10767.

The assay methods known in the prior art may utilize naturally occurring bioluminescent organisms, including *Photobacterium phosphoreum* and *Vibrio fischeri*. However, recent interest has focused on the use of genetically modified microorganisms which have been engineered to express bioluminescence. These genetically modified bioluminescent microorganisms usually express lux genes, encoding the enzyme luciferase, which have been cloned from a naturally occurring bioluminescent microorganism (E. A. Meighen (1994) Genetics of Bacterial Bioluminescence. *Ann. Rev. Genet.* 28: 117–139; Stewart, G. S. A. B. Jassin, S. A. A. and Denyer, S. P. (1993), Engineering Microbial bioluminescence and biosensor applications. In Molecular Diagnosis. Eds R. Rapley and M. R. Walker Blackwell Scientific Pubs/Oxford). A process for producing genetically modified bioluminescent microorganisms expressing lux genes cloned from *Vibrio harveyi* is described in U.S. Pat. No. 4,581,335.

The use of genetically modified bioluminescent microorganisms in toxicity testing applications has several advantages over the use of naturally occurring microorganisms. For example, it is possible to engineer microorganisms with different sensitivities to a range of different toxic substances or to a single toxic substance. However, genetically modified microorganisms are subject to marketing restrictions as a result of government legislation and there is major concern relating to the deliberate release of genetically modified microorganisms into the environment as components of commercial products. This is particularly relevant with regard to toxicity testing which is often performed in the field rather than within the laboratory. The potential risk from release of potentially pathogenic genetically modified microorganisms into the environment where they may continue to grow in an uncontrollable manner has led to the introduction of legal restrictions on the use of genetically modified organisms in the field in many countries.

It has been suggested, to avoid the problems discussed above, to use genetically modified bioluminescent microorganisms which have been treated so that they retain the metabolic function of bioluminescence but can no longer reproduce. The use of radiation (gamma-radiation), X-rays or an electron beam to kill bioluminescent cells whilst retaining the metabolic function of bioluminescence is demonstrated in International Patent Application Number WO 95/07346.

SUMMARY OF THE INVENTION

It is an object of the present invention to provide an alternative method of killing bioluminescent cells whilst retaining the metabolic function of bioluminescence which does not require the use of radiation and, as such, can be easily carried out without the need for specialized radiation equipment and containment facilities and without the risk to laboratory personnel associated with the use of radiation.

Accordingly, in a first aspect the invention provides a method of making a non-viable preparation of prokaryotic or eukaryotic cells, which preparation has a signal-generating metabolic activity, which method comprises contacting a viable culture of cells with signal-generating metabolic activity with a member of the bleomycin/phleomycin family of antibiotics.

Bleomycin and phleomycin are closely related glycopeptide antibiotics that are isolated in the form of copper chelates from cultures of *Streptomyces verticillus*. They represent a group of proteins with molecular weights ranging from 1000 to 10000 kda that are potent antibiotics and anti-tumour agents. So far more than 200 members of the bleomycin/phleomycin family have been isolated and characterised as complex basic glycopeptides. Family members resemble each other with respect to their physicochemical properties and their structure, indicating that functionally they all behave in the same manner. Furthermore, the chemical structure of the active moiety is conserved between family members and consists of 5 amino acids, L-glucose, 3-O-carbamoyl-D-mannose and a terminal cation. The various different bleomycin/phleomycin family members differ from each other in the nature of the terminal cation moiety, which is usually an amine. A preferred bleomycin/phleomycin antibiotic for use in the method of the invention is phleomycin D1, sold under the trade name Zeocin™.

Bleomycin and phleomycin are strong, selective inhibitors of DNA synthesis in intact bacteria and in mammalian cells. Bleomycin can be observed to attack purified DNA in vitro when incubated under appropriate conditions and analysis of the bleomycin damaged DNA shows that both single-stranded and double-stranded cleavages occur, the latter being the result of staggered single strand breaks formed approximately two base pairs apart in the complementary strands.

In in vivo systems, after being taken up by the cell, bleomycin enters the cell nucleus, binds to DNA (by virtue of the interaction between its positively charged terminal amine moiety and a negatively charged phosphate group of the DNA backbone) and causes strand scission. Bleomycin causes strand scission of DNA in viruses, bacteria and eukaryotic cell systems.

The present inventors have surprisingly found that treatment of a culture of cells with signal-generating metabolic activity with a bleomycin/phleomycin antibiotic renders the culture non-viable whilst retaining a level of signal-generating metabolic activity suitable for use in toxicity testing applications. In the context of this application the term non-viable is taken to mean that the cells are unable to reproduce. The process of rendering cells non-viable whilst retaining signal-generating metabolic activity may hereinafter be referred to as 'inactivation' and cells which have been rendered non-viable according to the method of the invention may be referred to as 'inactivated'.

Because of the broad spectrum of action of the bleomycin/phleomycin family of antibiotics the method of the invention is equally applicable to bacterial cells and to eukaryotic cells with signal generating metabolic activity. Preferably the signal-generating metabolic activity is bioluminescence but other signal-generating metabolic activities which are reporters of toxic damage could be used with equivalent effect.

The method of the invention is preferred for use with bacteria or eukaryotic cells that have been genetically modified to express a signal-generating metabolic activity. The examples given below relate to *E. coli* which have been engineered to express bioluminescence by transformation with a plasmid carrying lux genes. The eukaryotic equivalent would be cells transfected with a vector containing nucleic acid encoding a eukaryotic luciferase enzyme (abbreviated luc) such as, for example, luciferase from the firefly *Photinus pyralis*. A suitable plasmid vector containing cDNA encoding firefly luciferase under the control of an SV40 viral promoter is available from Promega Corporation, Madison Wis., USA. However, in connection with the present invention it is advantageous to use recombinant cells containing the entire eukaryotic luc operon so as to avoid the need to add an exogenous substrate ( e.g. luciferin) in order to generate light output.

The optimum concentration of bleomycin/phleomycin antibiotic and contact time required to render a culture of cells non-viable whilst retaining a useful level of signal-generating metabolic activity may vary according to the cell type but can be readily determined by routine experiment. In general, the lower the concentration of antibiotic used the longer the contact time required for cell inactivation. In connection with the production of assay reagents for use in toxicity testing applications, it is generally advantageous to keep the concentration of antibiotic low (e.g. around 1–1.5 mg/ml) and increase the contact time for inactivation. As will be shown in Example 1, treatment with Zeocin™ at a concentration of 1.5 mg/ml for 3 to 5 hours is sufficient to completely inactivate a culture of recombinant *E. coli*.

In the case of bacteria, the contact time required to inactivate a culture of bacterial cells is found to vary according to the stage of growth of the bacterial culture at the time the antibiotic is administered. Although the method of the invention can be used on bacteria at all stages of growth it is generally preferable to perform the method on bacterial cells in an exponential growth phase because the optimum antibiotic contact time has been observed to be shortest when the antibiotic is administered to bacterial cells in an exponential growth phase.

Following treatment with bleomycin/phleomycin antibiotic the non-viable preparation of cells is preferably stabilised for ease of storage or shipment. The cells can be stabilised using known techniques such as, for example, freeze drying (lyophilization) or other cell preservation techniques known in the art. Stabilization by freeze drying has the added advantage that the freeze drying procedure itself can render cells non-viable. Thus, any cells in the preparation which remain viable after treatment of the culture with bleomycin/phleomycin antibiotic will be rendered non-viable by freeze drying. It is thought that freeze drying inactivates any remaining viable cells by enhancing the effect of antibiotic, such that sub-lethally injured cells in the culture are more sensitive to the stresses applied during freeze drying.

Prior to use the stabilised cell preparation is reconstituted using a reconstitution buffer to form an assay reagent. This reconstituted assay reagent may then be used directly in assays for analytes, for example in toxicity testing applications. It is preferable that the stabilised (i.e. freeze dried) assay reagent be reconstituted immediately prior to use, but after reconstitution it is generally necessary to allow sufficient time prior to use for the reconstituted reagent to reach a stable, high level of signal-generating activity. Suitable reconstitution buffers preferably contain an osmotically potent non-salt compound such as sucrose, dextran or polyethylene glycol, although salt based stabilisers may also be used.

Whilst the assay reagent of the invention is particularly suitable for use in toxicity testing applications it is to be understood that the invention is not limited to assay reagents for use in toxicity testing. The cell inactivation method of the invention can be used to inactivate any recombinant cells (prokaryotic or eukaryotic) with a signal generating metabolic activity that is not dependent upon cell viability.

In a further aspect the invention provides a method of assaying a potentially toxic analyte comprising the steps of, (a) contacting a sample to be assayed for the analyte with a sample of assay reagent comprising a non-viable preparation of cells with a signal-generating metabolic activity;

(b) measuring the level of signal generated; and (c) using the measurement obtained as an indicator of the toxicity of the analyte.

In a still further aspect, the invention provides a kit for performing the above-stated assay comprising an assay reagent with signal generating metabolic activity and means for contacting the assay reagent with a sample to be assayed for an analyte.

The analytes tested using the assay of the invention are usually toxic substances, but it is to be understood that the precise nature of the analyte to be tested is not material to the invention.

Toxicity is a general term used to describe an adverse effect on biological system and the term 'toxic substances' includes both toxicants (synthetic chemicals that are toxic) and toxins (natural poisons). Toxicity is usually expressed as an effective concentration (EC) or inhibitory concentration (IC) value. The EC/IC value is usually denoted as a percentage response e.g. $EC_{50}$, $EC_{10}$ which denotes the concentration (dose) of a particular substance which affects the designated criteria for assessing toxicity (i.e. a behavioural trait or death) in the indicated proportion of the population tested. For example, an $EC_{50}$ of 10 ppm indicates that 50% of the population will be affected by a concentration of 10 ppm. In the case of a toxicity assay based on the use of a bioluminescent assay reagent, the $EC_{50}$ value is usually the concentration of sample substance causing a 50% change in light output.

The present invention will be further understood by way of the following Examples with reference to the accompanying Figures in which:

BRIEF DESCRIPTION OF THE DRAWINGS

FIG. 3: Control cells, lag phase.
FIG. 4: Zeocin™ treated cells, lag phase.
FIG. 5: Control cells, mid-exponential growth.
FIG. 6: Zeocin™ treated cells, mid-exponential growth.
FIG. 7: Control cells, stationary phase.
FIG. 8: Zeocin™ treated cells, stationary phase.

EXAMPLES

Example 1

(A) Inactivation of Bioluminescent *E. coli* Method

1. Bioluminescent genetically modified *E. coil* strain HB101 (*E. coli* HB101 made bioluminescent by transformation with a plasmid carrying the lux operon of *Vibrio fischeri* constructed by the method of Shaw and Kado, as described in Biotechnology 4: 560–564) were grown from a frozen stock in 5 ml of low salt medium (LB (5 g/ml NaCl)+glycerol+$MgSO_4$) for 24 hours.

2. 1 ml of the 5 ml culture was then used to inoculate 200 ml of low salt medium in a shaker flask and the resultant culture grown to an $OD_{630}$ of 0.407 (exponential growth phase).

3. 50 ml of this culture was removed to a fresh sterile shaker flask (control cells).

4. Zeocin™ was added to the 150 ml of culture in the original shaker flash, to a final concentration of 1.5 mg/ml. At the same time, an equivalent volume of water was added to the 50 ml culture removed from the original flask (control cells).

5. The time course of cell inactivation was monitored by removing samples from the culture at 5, 60, 120, 180, 240 and 300 minutes after the addition of Zeocin™ and taking measurements of both light output (measured using a Delta-tox luminometer) and viable count (per ml, determined using the method given in Example 3 below) for each of the samples. Samples of the control cells were removed at 5 and 300 minutes after the addition of water and measurements of light output and viable count taken as for the Zeocin™ treated cells.

Figure 1:
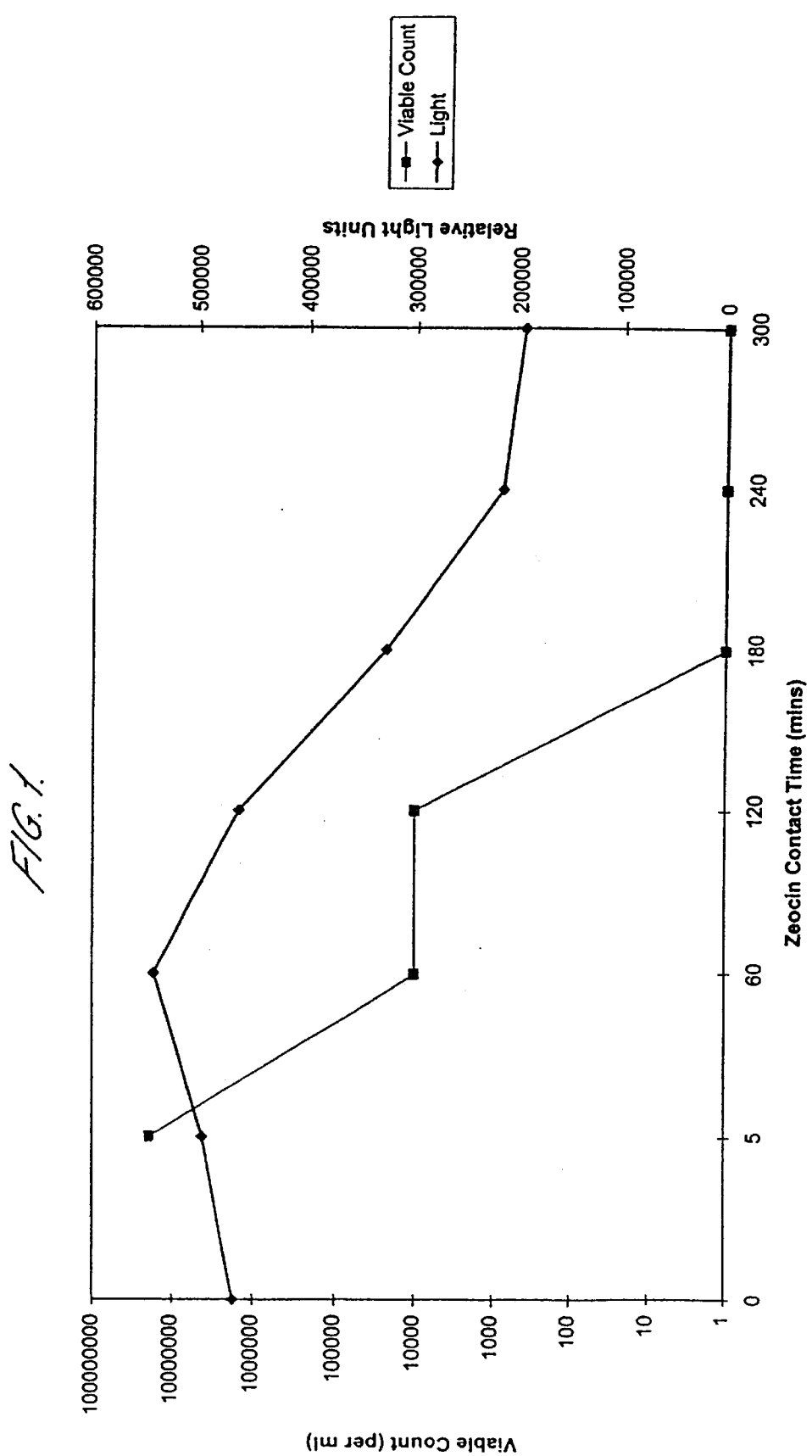
FIG. 1 is a graph to show the effect of Zeocin™ treatment on viable count and light output of recombinant bioluminescent *E. coil* cells.

FIG. 1 shows the effect of Zeocin™ treatment on the light output and viable count (per ml) of recombinant bioluminescent *E. coil*. Zeocin™ was added to a final concentration of 1.5 mg/ml at time zero. The number of viable cells in the culture was observed to decrease with increasing contact cells with Zeocin™, the culture being completely inactivated after 3 hours. The light output from the culture was observed to decrease gradually with increasing Zeocin™ contact time.

(B) Production of Assay Reagent

Five hours after the addition of Zeocin™ or water the remaining bacterial cells in the Zeocin™ treated and control cultures were harvested by the centrifugation, washed (to remove traces of Zeocin™ from the Zeocin™ treated culture), re-centrifuged and resuspended in cryoprotectant to an $OD_{630}$ of 0.25. 200 µl aliquots of the cells in cryoprotectant were dispensed into single shot vials, and freeze dried. Freeze dried samples of the Zeocin™ treated cells and control cells were reconstituted in 0.2M sucrose to form assay reagents and the light output of the assay reagents measured at various times after reconstitution.

The light output from assay reagent prepared from cells exposed to 1.5 mg/ml Zeocin™ for 5 hours was not significantly different to the light output from assay reagent prepared from control (Zeocin™ untreated) cells, indicating that Zeocin™ treatment does not affect the light output of the reconstituted freeze dried assay reagent. Both Zeocin™ treated and Zeocin™ untreated assay reagents produced stable light output 15 minutes after reconstitution.

Figure 2:
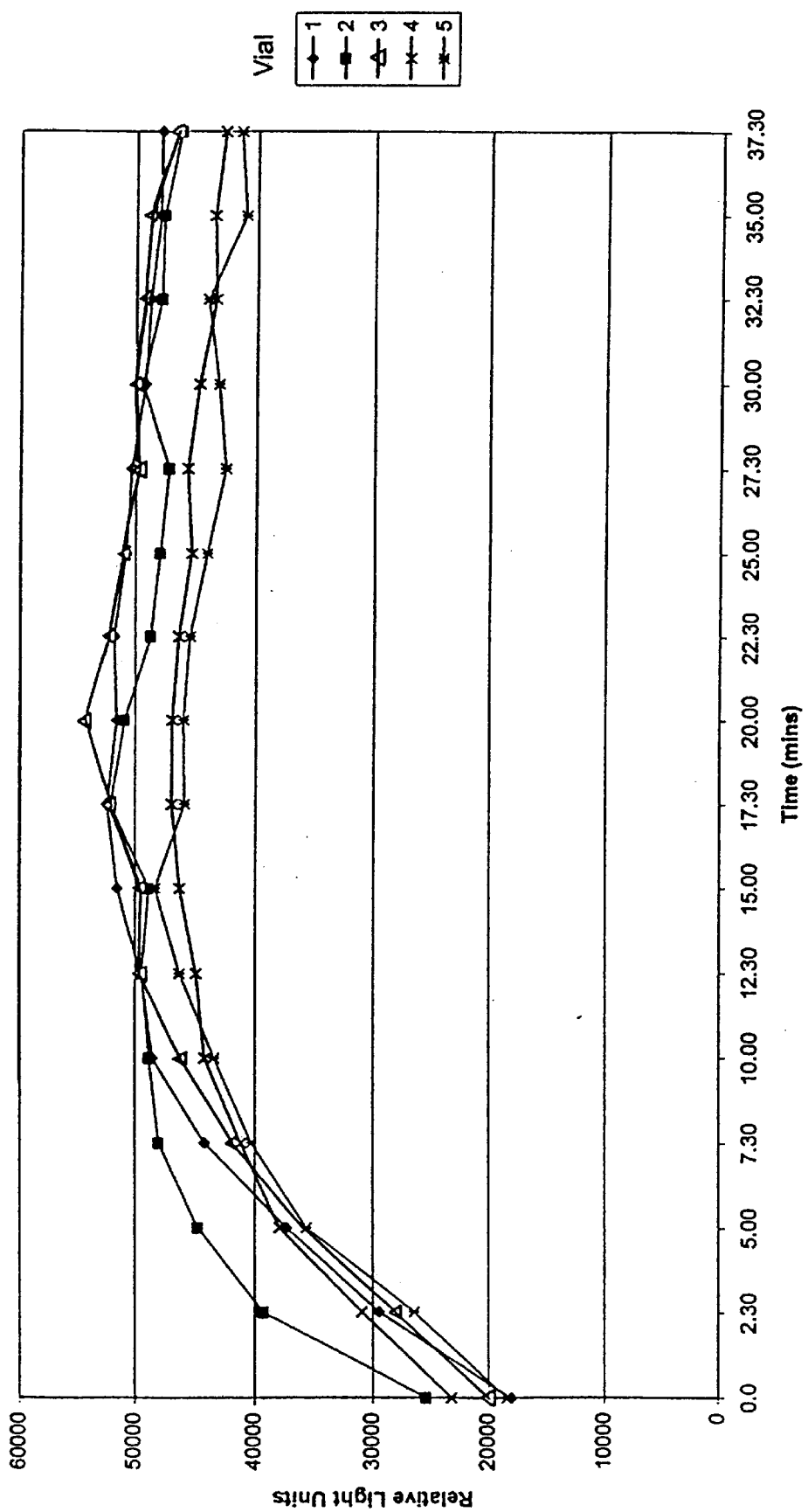
FIG. 2 is a graph to show the light output from five separate vials of reconstituted assay reagent. The assay reagent was prepared from recombinant bioluminescent *E. coil* exposed to 1.5 mg/ml Zeocin™ for 300 minutes. Five vials were used to reduce discrepancies resulting from vial to vial variation.

FIG. 2 shows the light output from five separate vials of reconstituted Zeocin™ treated assay reagent inactivated according to the method of Example 1(A) and processed into assay reagent as described in Example 1(B). Reconstitution solution was added at time zero and thereafter light output was observed to increase steadily before stabilising out at around 15 minutes after reconstitution. All five vials were observed to give similar light profiles after reconstitution.

Example 2

Sensitivity of Zeocin™ Treated Assay Reagent to Toxicant Method

1. Bioluminescent genetically modified *E. coil* strain HB101 (*E. coli* HB101 made bioluminescent by transformation with a plasmid carrying the lux operon of *vibrio fischeri* constructed by the method of Shaw and Kado, as described in Biotechnology 4: 560–564) was grown in fermenter as a batch culture in low salt medium (LB(5 g/ml NaCl)+glycerol+$MgSO_4$).

2. Two aliquots of the culture were removed from the fermenter into separate sterile shaker flasks at each of three different stages of growth i.e. at $OD_{630}$ values of 0.038 (lag phase growth), 1.31 (mid-exponential phase growth) and 2.468 (stationary phase growth).

3. One aliquot of culture for each of the three growth stages was inactivated by contact with Zeocin™ (1 mg Zeocin™ added per $2.5 \times 10^6$ cells, i.e. the concentration of Zeocin™ per cell is kept constant) for 300 minutes and then processed into assay reagent by freeze drying and reconstitution, as described in part (B) of Example 1.

4. An equal volume of water was added to the second aliquot of culture for each of the three growth stages and the cultures processed into assay reagent as described above.

5. Samples of each of the three Zeocin™ treated and three control assay reagents were then evaluated for sensitivity to toxicant ($ZnSO_4$) according to the following assay protocol:

$ZnSO_4$ Sensitivity Assay

1. $ZnSO_4$ solutions were prepared in pure water at 30, 10, 3, 1, 0.3 and 0.1 ppm. Pure water was also used as a control.

2. Seven vials of each of the three Zeocin™ treated and each of the three control assay reagents (i.e. one for each of the six $ZnSO_4$ solutions and one for the pure water control) were reconstituted using 0.5 ml of reconstitution solution (eg 0.2M sucrose) and then left to stand at room temperature for 15 minutes to allow the light output to stabilize. Base line (time zero) readings of light output were then measured for each of the reconstituted reagents.

3. 0.5 ml aliquots of each of the six ZnSO$_4$ solutions and the pure water control were added to separate vials of reconstituted assay reagent. This was repeated for each of the different Zeocin™ treated and control assay reagents.

4. The vials were incubated at room temperature and light output readings were taken 5, 10, 15, 20, 25 and 30 minutes after addition of ZnSO$_4$ solution.

Figure 3:
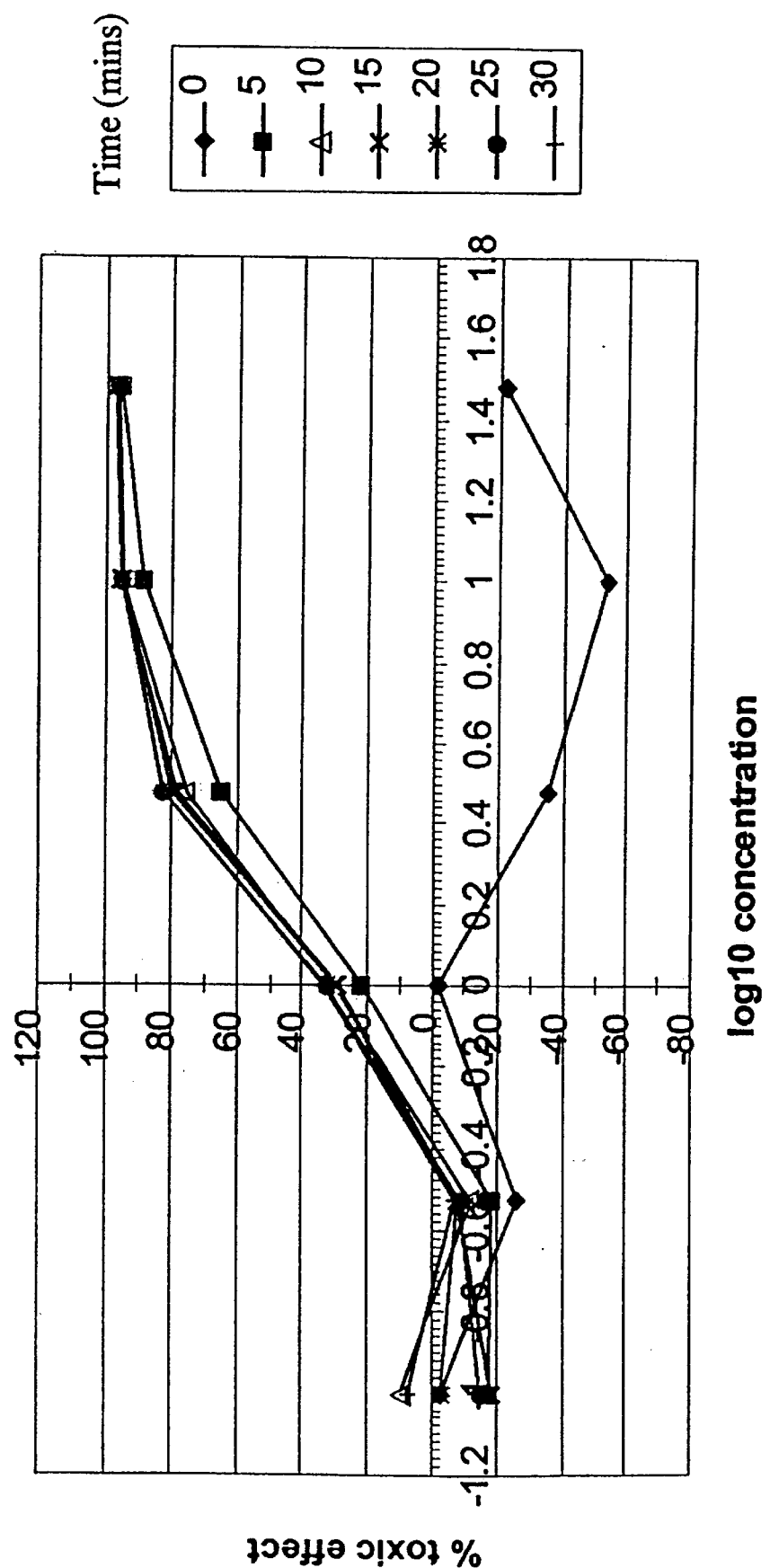
FIGS. 3 to 8 are graphs to show the effect of Zeocin™ treatment on the sensitivity of bioluminescent assay reagent to toxicant ($ZnSO_4$)
Figure 4:
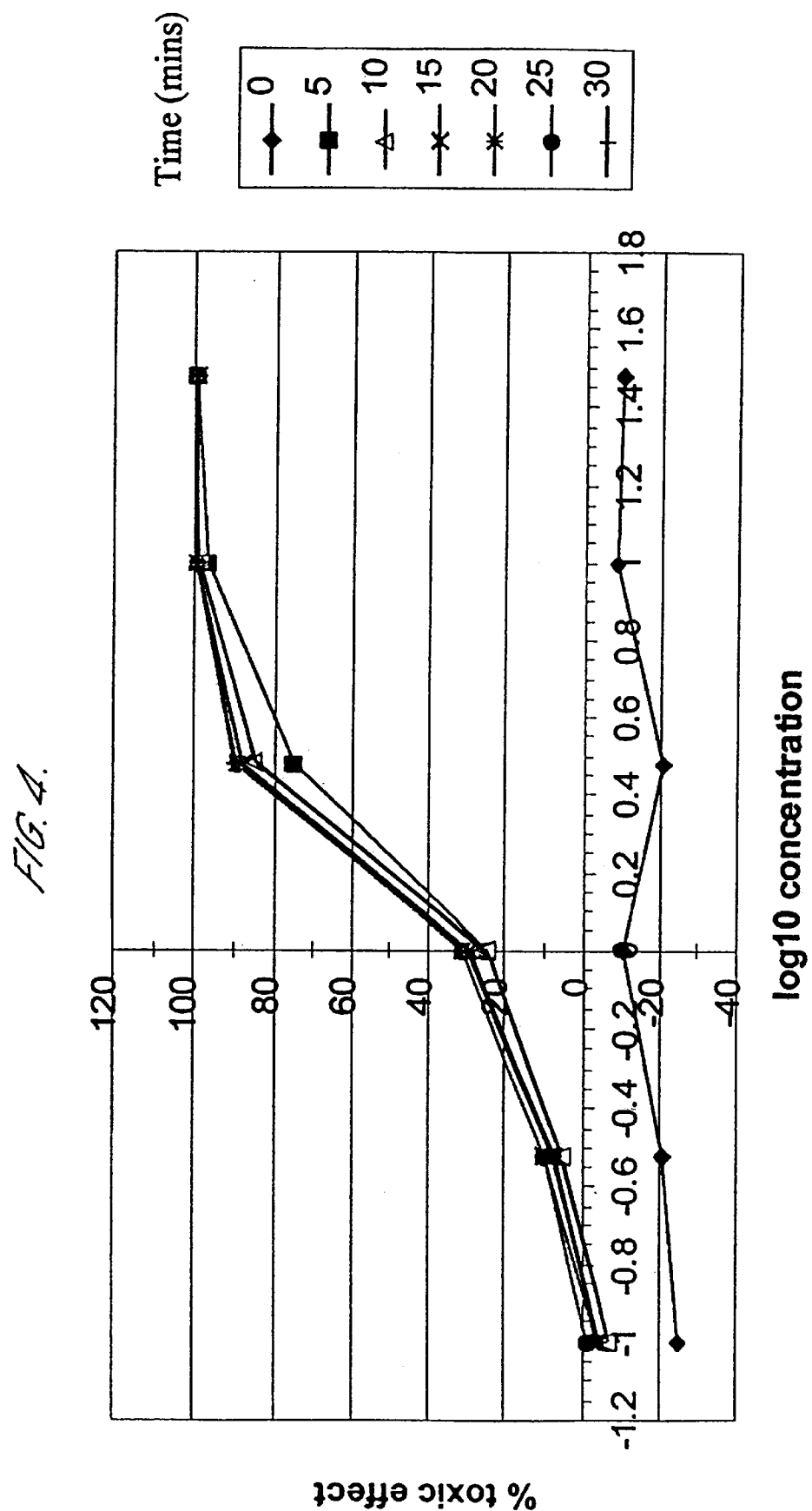
Figure 5:
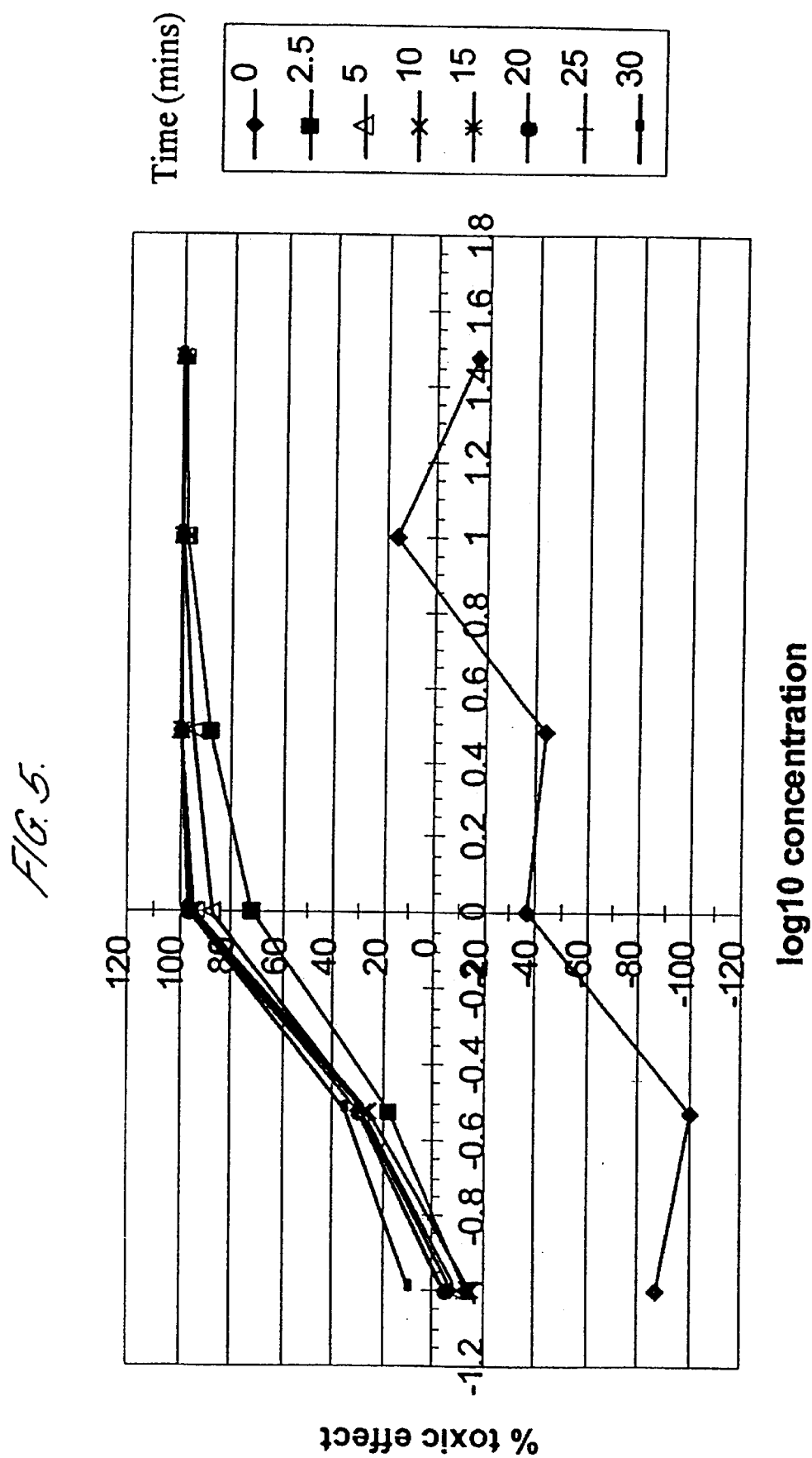
Figure 6:
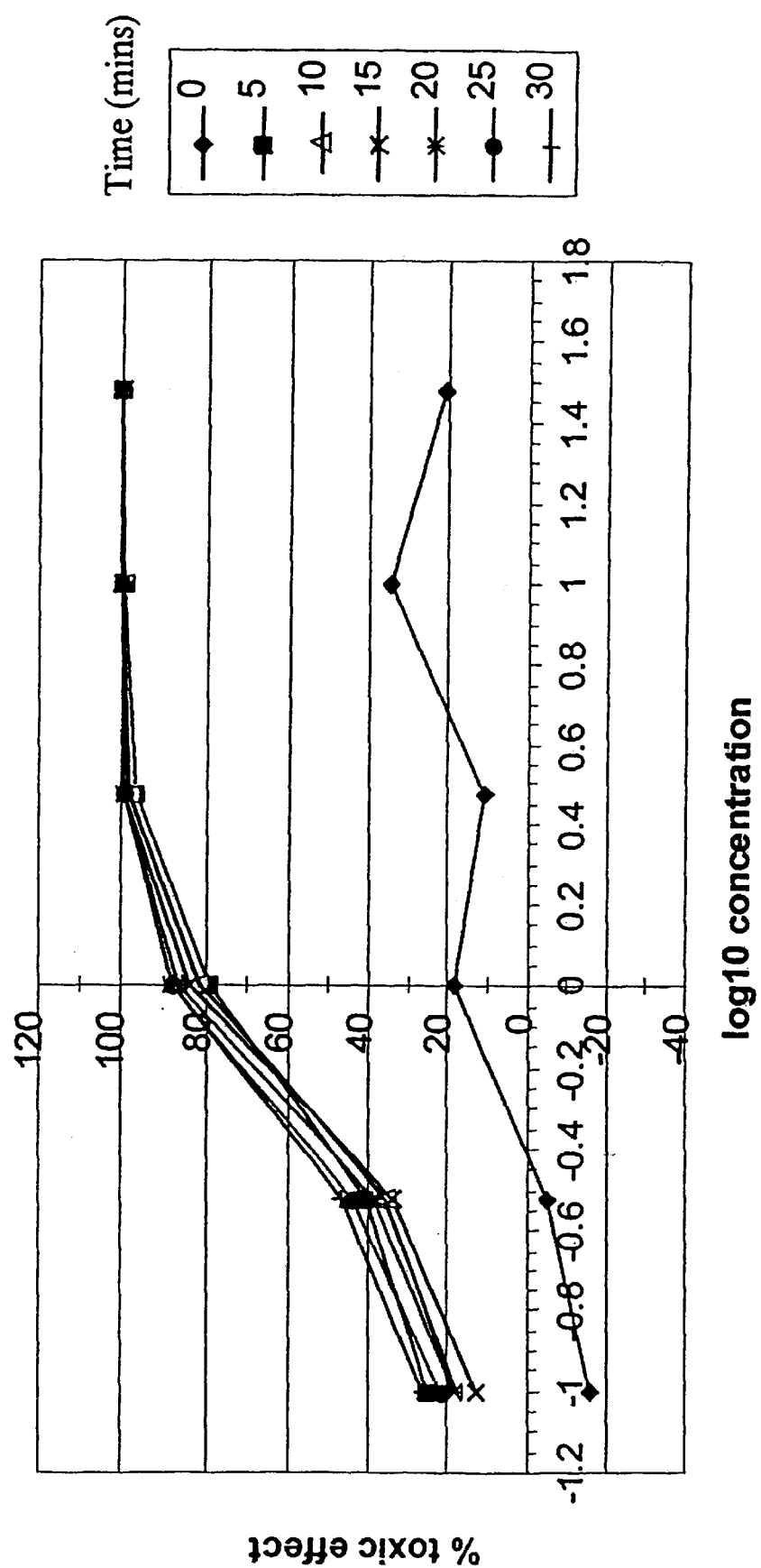
Figure 7:
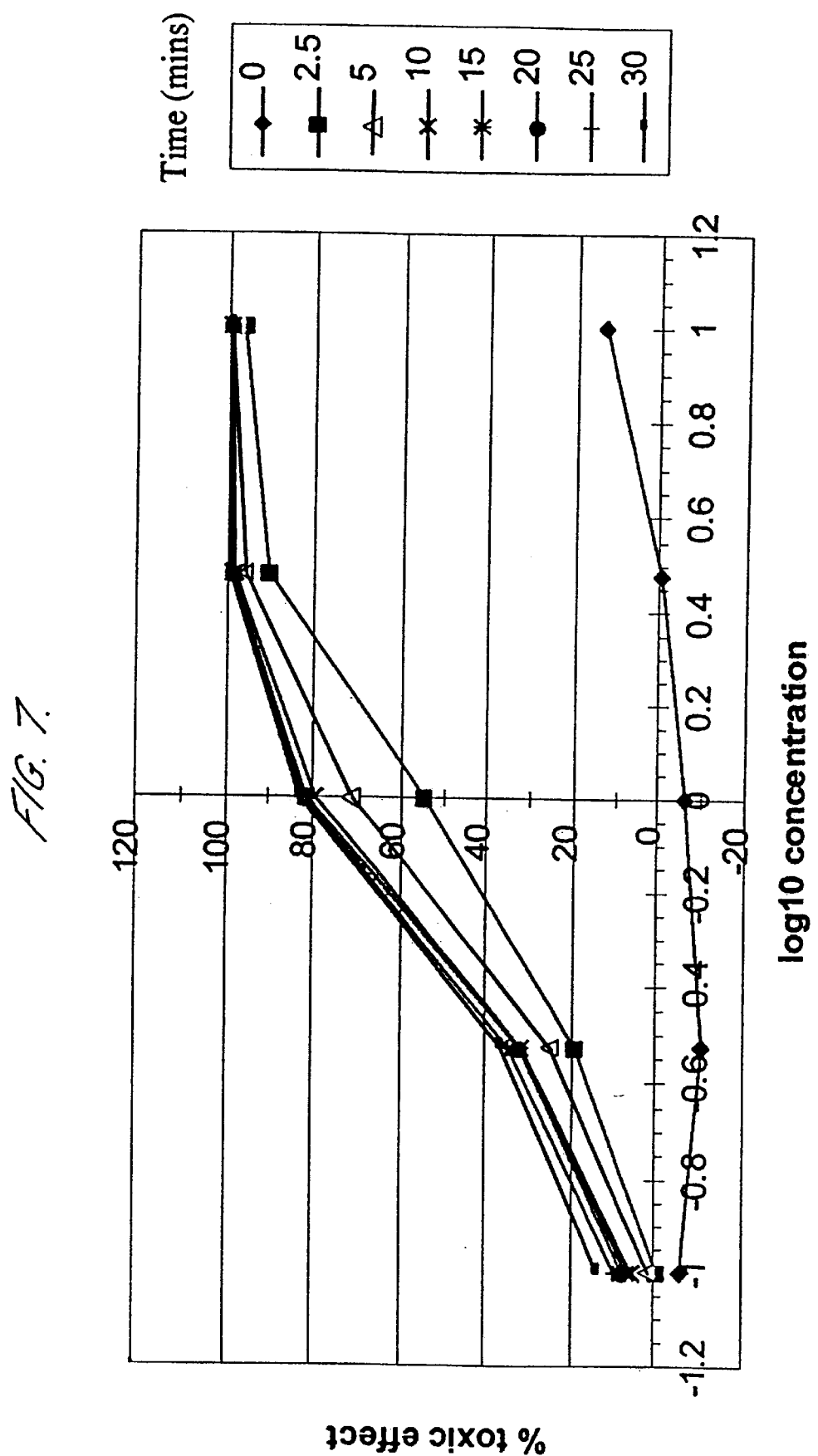
Figure 8:
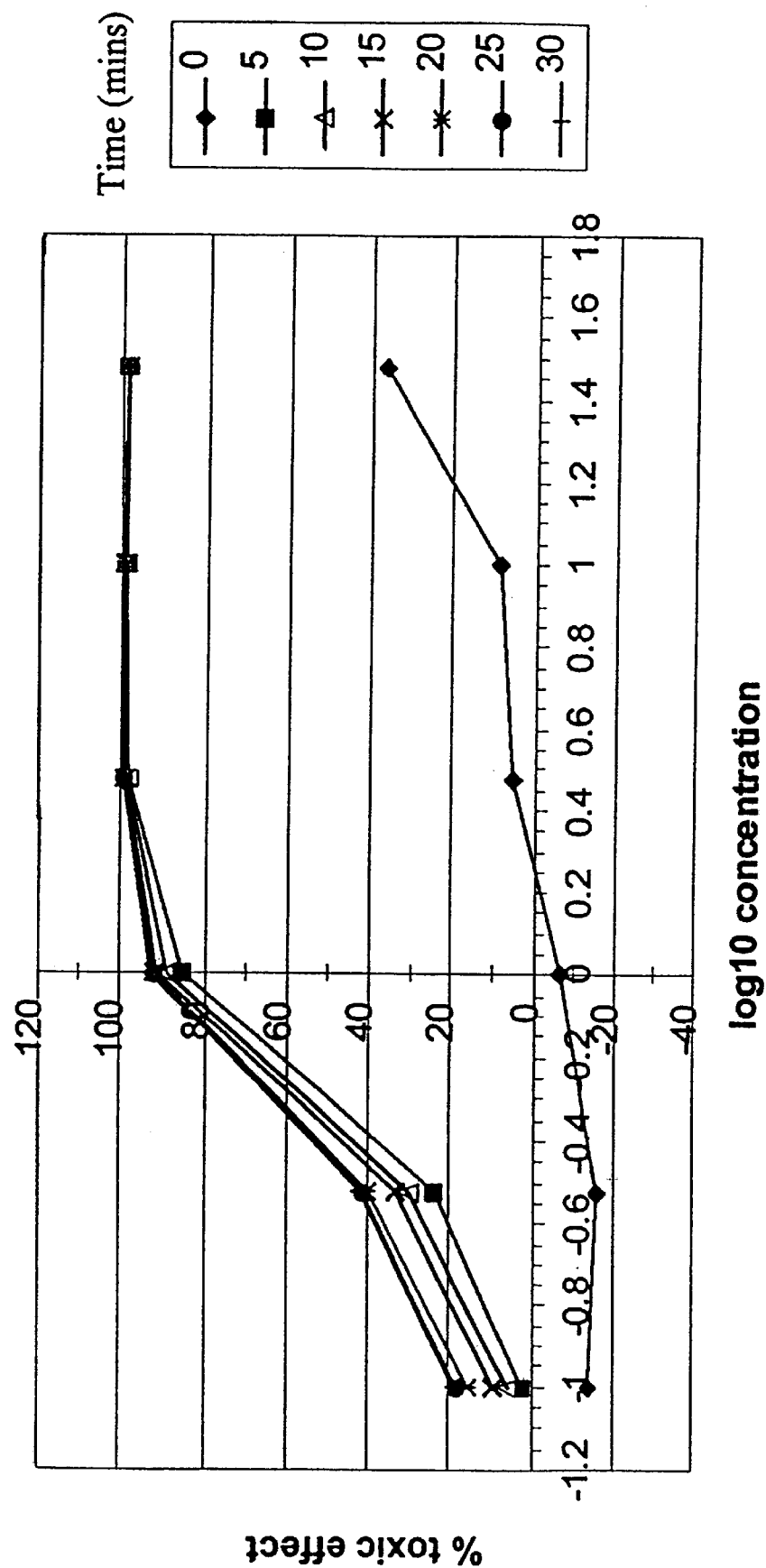

5. The % toxic effect for each sample was calculated as follows:

$$\% \text{ toxic effect} = 1 - \left(\frac{S_c \times C_o}{S_o \times C_t}\right) \times 100$$

where: $C_o$=light in control at time zero
$C_t$=light in control at reading time
$S_o$=light in sample at time zero
$S_t$=light in sample at reading time The results of toxicity assays for sensitivity to ZnSO$_4$ for all the Zeocin™ treated and control assay reagents are shown in FIGS. 3 to 8:

FIG. 3: Control cells, lag phase.
FIG. 4: Zeocin™ treated cells, lag phase.
FIG. 5: Control cells, mid-exponential growth.
FIG. 6: Zeocin™ treated cells, mid-exponential growth.
FIG. 7: Control cells, stationary phase.
FIG. 8: Zeocin™ treated cells, stationary phase.

In each case, separate graphs of % toxic effect against $\log_{10}$ concentration of ZnSO$_4$ were plotted on the same axes for each value of time (minutes) after addition of Zeocin™ or water. The sensitivities of the various reagents, expressed as an EC$_{50}$ value for 15 minutes exposed to ZnSO$_4$, are summarised in Table 1 below.

TABLE 1

Sensitivity of the different assay reagents to ZnSo$_4$ expressed as EC$_{50}$ values for 15 minutes exposure to ZNSO$_4$.

| GROWTH STAGE OF ASSAY REAGENT | SENSITIVITY-EC$_{50}$ VALUES | |
|---|---|---|
| | ZEOCIN ™ TREATED | CONTROL CELLS |
| Lag Phase | 1.445 ppm ZnSO$_4$ | 1.580 ppm ZnSO$_4$ |
| Expotential phase | 0.446 ppm ZnSO$_4$ | 0.446 ZnSO$_4$ |
| Stationary phase | 0.426 ppm ZnSO$_4$ | 0.457 ppm ZnSO$_4$ |

The results of the toxicity assays indicate that Zeocin™ treatment does not significantly affect the sensitivity of a recombinant bioluminescent *E. coli* derived assay reagent to ZnSO$_4$. Similar results could be expected with other toxic substances which have an effect on signal-generating metabolic activities.

Example 3

Method to Determine Viable Count

1. Samples of bacterial culture to be assayed for viable count were centrifuged at 10,000 rpm for 5 minutes to pellet the bacterial cells.

2. Bacterial cells were washed by resuspending in 1 ml of M9 medium, re-centrifuged at 10,000 rpm for 5 minutes and finally re-suspended in 1 ml of M9 medium.

3. Serial dilutions of the bacterial cell suspension from $10^{-1}$ to $10^{-7}$ were prepared in M9 medium.

4. Three separate 10 μl aliquots of each of the serial dilutions were plated out on standard agar plates and the plates incubated at 37° C.

5. The number of bacterial colonies present for each of the three aliquots at each of the serial dilutions were counted and the values averaged. Viable count was calculated per ml of bacterial culture.

What is claimed is:

1. A method of making a non-viable preparation of prokaryotic cells, which preparation has a bioluminescent signal-generating metabolic activity, which method comprises contacting a viable culture of a genetically modified *E. coli* strain made bioluminescent by transformation with a plasmid carrying the lux operon of *Vibrio fischeri* with an antibiotic selected from the bleomycin/phleomycin family of antibiotics.

2. The method as claimed in claim 1, wherein said antibiotic is phleomycin D1.

3. The method as claimed in claim 2 wherein said cells are contacted with phleomycin D1 at a concentration of at least about 1.5 mg/ml.

4. The method as claimed in claim 3 wherein said contact is maintained for at least about 3 hours.

5. The method as claimed in claim 4 wherein said antibiotic-treated cells are harvested, washed and freeze-dried.

6. The method as claimed in claim 1, wherein following contact with the antibiotic, said cells are subjected to a stabilization step.

7. The method as claimed in claim 6 wherein said stabilization step comprises freeze drying.

8. The method as claimed in claim 1, wherein said culture of genetically modified *E. Coli* strain comprises cells that are in an exponential growth phase when contacted with said antibiotic.

* * * * *